US008242096B2

(12) United States Patent
Chen et al.

(10) Patent No.: US 8,242,096 B2
(45) Date of Patent: Aug. 14, 2012

(54) COMPOSITIONS COMPRISING PECTIN AND ASCORBIC ACID

(75) Inventors: Chyi-Cheng Chen, Binningen (CH); Bruno Leuenberger, Allschwil (CH)

(73) Assignee: DSM IP Assets B.V., TE Heerlen (NL)

(*) Notice: Subject to any disclaimer, the term of this patent is extended or adjusted under 35 U.S.C. 154(b) by 244 days.

(21) Appl. No.: 12/378,306

(22) Filed: Feb. 13, 2009

(65) Prior Publication Data

US 2009/0227536 A1 Sep. 10, 2009

Related U.S. Application Data

(63) Continuation of application No. 10/488,451, filed as application No. PCT/EP02/09484 on Aug. 24, 2002, now abandoned.

(30) Foreign Application Priority Data

Sep. 3, 2001 (EP) .................................. 01121067.1

(51) Int. Cl.
*A01N 61/00* (2006.01)
*A01N 51/00* (2006.01)
(52) U.S. Cl. .............................. 514/54; 514/1; 514/157
(58) Field of Classification Search ................... 424/489
See application file for complete search history.

(56) References Cited

U.S. PATENT DOCUMENTS

| | | | |
|---|---|---|---|
| 3,312,594 | A | 4/1967 | Norman et al. |
| 3,459,863 | A | 8/1969 | Apelian et al. |
| 3,490,742 | A | 1/1970 | Nichols et al. |
| 3,615,591 | A | 10/1971 | Newlin et al. |
| 3,778,510 | A | 12/1973 | Blonde |
| 3,946,110 | A | 3/1976 | Hill |
| 4,225,628 | A | 9/1980 | Lynn |
| 4,372,968 | A | 2/1983 | Kitamori et al. |
| 4,533,674 | A | 8/1985 | Schmidt et al. |
| 4,605,666 | A | 8/1986 | Schmidt et al. |
| 5,008,254 | A | 4/1991 | Weibel |
| 6,060,078 | A | 5/2000 | Lee |
| 6,123,963 | A | 9/2000 | Kim et al. |
| 6,136,347 | A | 10/2000 | Pollinger et al. |
| 6,217,903 | B1 | 4/2001 | Skinner |

FOREIGN PATENT DOCUMENTS

| | | |
|---|---|---|
| EP | 0 089 056 A2 | 3/1983 |
| EP | 0 875 245 A2 | 11/1998 |
| EP | 1 110 550 A2 | 6/2001 |
| EP | 1110550 A2 * | 6/2001 |
| FR | 2 036 890 | 12/1970 |
| GB | 1109186 | 4/1968 |
| WO | WO 99/06029 | 2/1999 |

OTHER PUBLICATIONS

Varanyanond et al., Changes in Pectin Content and Average Molecular Weight of Pectin during Maturation of the Mango "Kaew", Food Sci. Technol. Res. 5(4), 362-364, 1999, especially pp. 362 and 363).*
Derwent Publications Abstract No. XP-002233557 of Lyubenko, P. et al., Application No. 1994-277493 (RU 2 008 015 (Feb. 28, 1994)).
Bi Dianzhou, et al., Pharmacy, 4th Ed., p. 346, People's Healthy Press (1999).
Zheng Junmin et al., Science and Technology of Pharmaceutical Polymer Materials, p. 51, line 24 (1996).
English translation of Bi Dianzhou, et al., Pharmacy, 4th Ed., p. 346, People's Healthy Press (1999).
English translation of Zheng Junmin et al., Science and Technology of Pharmaceutical Polymer Materials, p. 51, line 24 (1996).
Mr. Myatts Wellness Club, Modified Citrus Pectin, http://www.drmyattswellnessclub.com/modcitruspectin.htm, (2007), printed pp. 1-3.
Varanyanond, et al. Changes in Pectin Content and Average Molecular Weight of Pectin . . . Food Sci. Technol. Res. 5(4), 1999, 362-364.
Solaray Super Bio-Plex Vitamin C & Bioflavonoids, www.vitamins-etc.com, 1999.
GNC A-Z Chewable C 500mg with Cirturc C Complex, Fruit Flavor Tablets, Product Information Brochure, www.drugstore.com, 1999.
Total C Product Information Brochure, www.nutripeak.com, 1998.
A Guide to Halal Food Selection, Hussaini et al., 1993.
Chiralt et al., Combined vacuum impregnation-osmotic dehydration in cryoprotection of apple, 1999, IFT Annual Meeting.
Derwent English language abstract of EP 0 089 056 A2 (Document B1 above).
Derwent English language abstract of FR 2 036 890 (Document B4 above).
Derwent English language abstract of DE 19733094. A foreign counterpart to WO 99/06029 (Document B6 above).
Food Technology Dictionary, pp. 574-575, with attached English Translation of "fluidized bed dryer".
Ginter, E. et al., "Natural Hypocholesterolemic Agent: Pectin plus Ascorbic Acid," Internat. J. Vit. Nutr. Res., vol. 49(4) pp. 406-412 (1979).
Vozar, J. et al., "Effects of Pectin and Ascorbic Acid upon Glucose Tolerance and the Serum Lipid Levels," Vnitrni Lek., vol. 26(12) pp. 1183-1189 (1980).
Sadeghi et al., "Effect of Particle Size, Compaction Force and Presence of Aeorosil 200 on the Properties of Matrices Prepared from Physical Mixture of Propranolol Hydrochloride and Eudragit RS or RL", Iranian Journal of Basic Medical Sciences, vol. 10, pp. 197-205 (2007).

\* cited by examiner

*Primary Examiner* — Sreeni Padmanabhan
*Assistant Examiner* — Timothy E Betton
(74) *Attorney, Agent, or Firm* — Bryan Cave LLP

(57) ABSTRACT

Ascorbic acid compositions in the form of a powder and/or granules contain as principle components L-ascorbic acid and/or a pharmaceutically acceptable salt thereof, and a high molecular (300 kDalton or higher) pectin. The compositions are compressible into tablets with improved mechanical strength and hardness.

17 Claims, No Drawings

COMPOSITIONS COMPRISING PECTIN AND ASCORBIC ACID

This application is a continuation of U.S. application Ser. No. 10/488,451, filed Mar. 3, 2004 now abandoned, which is the National Stage of International Application No. PCT/EP02/09484, filed Aug. 24, 2002, which claims the benefit of EP 01121067.1, filed Sep. 3, 2001.

The present invention relates to a composition in the form of a powder and/or granules, which contain as principal components L-ascorbic acid and/or a pharmaceutically acceptable salt thereof, and high molecular pectin. The composition according to the present invention is directly compressible into tablets with good taste, improved mechanical strength and hardness, with excellent color stability and is free of sugar and starch. The addition of adjuvants and excipients to the composition for producing tablets is optional.

Compositions comprising L-ascorbic acid and/or a pharmaceutically acceptable salt thereof and pectin, as well as tablets manufactured using such compositions have been described in European Patent Application No. 1 110 550 A2.

It has now been found that tablets manufactured using a composition comprising L-ascorbic acid and/or its salts, and high molecular pectin show improved hardness as compared to tablets manufactured using conventional pectin of lower molecular weight.

Thus, in one aspect the invention relates to a composition in the form of a powder or granules comprising:

(a) L-ascorbic acid and/or a pharmaceutically acceptable salt thereof, (b) high molecular pectin and, optionally, (c) adjuvants and excipients.

The term "high molecular pectin" as used herein denotes pectin having an average molecular weight of about 300 kDalton or higher. The preferred high molecular pectins are those having an average molecular weight of from about 300 kDalton to about 400 kDalton, particularly 350 kDalton. Such pectins can be obtained as disclosed in U.S. Pat. No. 6,143,337 (inventors: Marshall L. Fishman and Hoa K. Chau, assignors to The United States of America as represented by the Secretary of Agriculture) the contents of which is incorporated herein by reference. The average molecular weight is determined by size exclusion chromatography having a multi angle laser light scattering detector as described in U.S. Pat. No. 6,143,337. However, pectins of higher molecular weight, e.g. up to 2000 kDalton can be used also in the present invention. Pectins of such molecular weight can be obtained e.g. from *Asteraceae* plants, especially cichory and Jerusalem artichoke, see International patent application WO 99/03892. Fractions of the desired high molecular weight can be obtained from such pectins by membrane filtration, e.g. using polyethersulfone or composite regenerate cellulose membranes as supplied by Millipore Corporation, Bedford, Mass. 01730, USA, under the trade name Pellicon® Tangential Flow Filtration Cassettes.

In accordance with the present invention, the high molecular pectin is preferably used in quantities within the range of about 0.1% to about 10% by weight, preferably in quantities of about 0.5% to about 5% by weight and most preferably in quantities of about 0.5% to about 2% by weight, calculated to the total weight of the composition thereof. Experiments have shown that a composition consisting of 95-99% by weight of L-ascorbic acid and/or the pharmaceutically acceptable salt thereof and 5-1% by weight of pectin, the two components totaling 100% by weight, i.e. with no other components present, yield tablets of very good quality and excellent color stability.

Adjuvants may optionally be added. Suitable adjuvants are for example starch, HPMC, polyols. Preferably no adjuvants are added.

The composition of this invention may be produced by any method known per se for the production of powders or granules. Preferred are fluidized-bed granulation, high-shear granulation, extrusion, spray-drying and wet granulation.

For obtaining the composition of the present invention by spray-drying it is convenient to prepare an aqueous slurry of all the components. The slurry has preferably a solid content of about 10 to 70% by weight, and preferably about 30 to 70% by weight. The slurry is then spray-dried in a manner known per se.

For obtaining the composition of the present invention by fluidized-bed granulation it is convenient to use a known fluidized-bed granulating apparatus which comprises a fluidized-bed drying device fitted with spray means. Preferably the L-ascorbic acid and/or a pharmaceutically acceptable salt thereof form the fluidized bed, which is fluidized by air or an inert gas, e.g. nitrogen. The pectin, as well as optional adjuvants, dissolved in an appropriate amount of water and sprayed in the form of an atomized mist onto the fluidized particles in such a manner that the granulating and drying operations is accomplished in a single step. The granulating process is continued until the desired amount of the pectin binder has been deposited onto the fluidized particles. The granules are sieved to remove the fractions of granules which are either too large or too small. Preferably, the particle size of the granules is within 100 and 1000 micron, more preferably between 125 and 850 microns. While the so-obtained granules are substantially dry they may contain a very small percentage of water depending on the amount of pectin. For 1% pectin, the moisture content is about 0.2% or less. For 5% pectin, the moisture content may be as high as 1%.

The composition thus obtained may be compressed into tablets with conventional tabletting methods and machinery. Optionally the powder or the granules may further be mixed with a lubricant or a mixture of lubricants and then compressed into tablets. If additional lubricant is used it is preferably selected from the group of stearic acid or the magnesium or calcium salt thereof, or glyceryl behenate (Compritol 888 ATO), preferably in an amount of about 0.5 to 4% by weight, calculated to the total weight of the composition. Or the composition may be mixed with excipients. Examples for excipients are dextrinized sucrose (Di Pac sugar), microcrystalline cellulose or starch.

A single tablet as obtained according to the present invention contains preferably 50 mg to 1500 mg, preferably 500 mg to 1000 mg of L-ascorbic acid and/or the pharmaceutically acceptable salt thereof, corresponding to an appropriate daily dose of vitamin C. The following Example illustrates the invention further.

EXAMPLE

Two pectins having different molecular weight were investigated. One had an average molecular weight of 200 kDalton (USP/100, lot 02635-0, CP Kelco, San Diego, USA) and another had an average molecular weight of about 350 kDalton. The 350 kDalton pectin was a sample from the United States Department of Agriculture and was prepared by the process disclosed in U.S. Pat. No. 6,143,337.

A 1.9% pectin solution was prepared by dissolving pectin in water. Sodium ascorbate powder (F. Hoffmann—La Roche AG, Switzerland, Ave. particle size ca. 50 microns) was placed in a Glatt Fluidized-Bed granulator (Model Uniglatt, Switzerland) and sprayed with a fine mist of the pectin solution, which was kept at about 50° C. during spraying. The granulation conditions were as follows:

L-Sodium ascorbate: 400 g
1.9% Pectin solution: 213 g
Pectin solution spraying rate: 9.9 g/minute
Inlet air temperature: 80° C.
Outlet air temperature: 40° C.
Product temperature: 32° C.

The granules had a particle size distribution as shown in Table 1. The granules (125-850 micron fraction) were mixed with the excipients as shown in Table 2 and then compressed into 700-mg tablets with a diameter of 12 mm to tablets of various thickness. The hardness of the tablets was determined and is shown in Table 3.

TABLE 1

Particle Size Distribution, %

| | Particle Size (Microns) | | | | | | |
|---|---|---|---|---|---|---|---|
| | >850 | >710 | >500 | >355 | >250 | >125 | <125 |
| Pectin USDA (C99-482) | 8.5 | 6.2 | 17.2 | 20.8 | 21.0 | 20.2 | 6.1 |
| Pectin USP100 CP Kelco (lot 02635-0) | 15.3 | 6.1 | 14.1 | 16.8 | 19.8 | 21.0 | 7.0 |

TABLE 2

| | Parts |
|---|---|
| Granule sample prepared from the example | 100 |
| Roche Ascorbic Acid 90% Granulation | 65.84 |
| White Di Pac sugar | 249.04 |
| Compritol 888 ATO | 8.48 |

TABLE 3

| Pectin USDA (C99-482) Mol. Weight: 350 kDalton | | CP Kelco Pectin USP100 (lot 02635-0) Mol. Weight: 200 kDalton | |
|---|---|---|---|
| Tablet Thickness mm | Tablet Hardness N | Tablet Thickness mm | Tablet Hardness N |
| 4.30 | 146.6 | 4.31 | 134.3 |
| 4.15 | 202.3 | 4.16 | 175.5 |
| 4.05 | 238.6 | 4.04 | 208.5 |
| 3.98 | 255.0 | 3.98 | 234.8 |
| 3.94 | 268.6 | 3.93 | 243.1 |
| 3.97 | 297.4 | n.a. | n.a. | n.a.: not available

The results of Table 3 show that the use of the high molecular pectin (MW 350 kDalton) resulted in tablets of substantially higher hardness when the same or substantially the same tabletting parameters were applied.

What is claimed is:

1. A composition in the form of a powder or granules comprising:
    (a) L-ascorbic acid and/or a pharmaceutically acceptable salt thereof, and
    (b) pectin having an average molecular weight of about 300 kDalton or higher.

2. A composition according to claim 1, wherein the pectin has an average molecular weight of about 300 kDalton to about 400 kDalton.

3. A composition according to claim 1, wherein the pectin has an average molecular weight of about 350 kDalton.

4. A composition according to claim 1 wherein the L-ascorbic acid and/or a pharmaceutically acceptable salt thereof is sodium L-ascorbate.

5. A composition according to claim 1, wherein the pectin is present in quantities within the range of about 0.1% to about 10% by weight, calculated on the total weight of the composition.

6. A composition according to claim 1, wherein the pectin is present in quantities within about 0.5% to about 2% by weight, calculated on the total weight of the composition.

7. A composition according to claim 1, wherein said composition consists of 95-99% by weight of L-ascorbic acid and/or a pharmaceutically acceptable salt thereof and 5-1% by weight of pectin, the two components totaling 100% by weight.

8. A composition according to claim 1 in the form of a compressed tablet.

9. A composition according to claim 1 further comprising an adjuvant or excipient.

10. A composition according to claim 2 wherein the L-ascorbic acid and/or a pharmaceutically acceptable salt thereof is sodium L-ascorbate.

11. A composition according to claim 3 wherein the L-ascorbic acid and/or a pharmaceutically acceptable salt thereof is sodium L-ascorbate.

12. A composition according to claim 9 wherein the L-ascorbic acid and/or a pharmaceutically acceptable salt thereof is sodium L-ascorbate.

13. A composition according to claim 4, wherein the pectin is present in quantities within the range of about 0.1% to about 10% by weight, calculated on the total weight of the composition.

14. A composition according to claim 9, wherein the pectin is present in quantities within the range of about 0.1% to about 10% by weight, calculated on the total weight of the composition.

15. A composition according to claim 4, wherein the pectin is present in quantities within about 0.5% to about 2% by weight, calculated on the total weight of the composition.

16. A composition according to claim 4, wherein said composition consists of 95-99% by weight of sodium L-ascorbate and 5-1% by weight of pectin, the two components totaling 100% by weight.

17. A composition according to claim 4 in the form of a compressed tablet.

* * * * *